(12) United States Patent
Keefe et al.

(10) Patent No.: US 10,409,535 B2
(45) Date of Patent: Sep. 10, 2019

(54) NETWORKABLE MEDICAL LABELING APPARATUS AND METHOD

(71) Applicant: CODONICS, INC., Mlddleburg Heights, OH (US)

(72) Inventors: Gary Keefe, Brecksville, OH (US); Lawrence Srnka, Northfield Center, OH (US)

(73) Assignee: CODONICS, INC., Middleburg Heights, OH (US)

( * ) Notice: Subject to any disclaimer, the term of this patent is extended or adjusted under 35 U.S.C. 154(b) by 0 days.

(21) Appl. No.: 15/968,363

(22) Filed: May 1, 2018

(65) Prior Publication Data

US 2018/0314478 A1   Nov. 1, 2018

Related U.S. Application Data

(60) Provisional application No. 62/492,519, filed on May 1, 2017.

(51) Int. Cl.
| | |
|---|---|
| *H04N 1/04* | (2006.01) |
| *G06F 3/12* | (2006.01) |
| *G16H 10/60* | (2018.01) |
| *G06Q 30/06* | (2012.01) |
| *G06Q 50/22* | (2018.01) |
| *H04L 29/08* | (2006.01) |
| *G16H 20/17* | (2018.01) |

(52) U.S. Cl.
CPC .......... *G06F 3/1255* (2013.01); *G06F 3/1204* (2013.01); *G06F 3/125* (2013.01); *G06F 3/1208* (2013.01); *G06F 3/1243* (2013.01); *G06F 3/1285* (2013.01); *G06Q 30/06* (2013.01); *G16H 10/60* (2018.01); *G06Q 50/22* (2013.01); *G16H 20/17* (2018.01); *H04L 67/12* (2013.01)

(58) Field of Classification Search
CPC ....... G06F 3/1225; G06F 3/1208; G06F 3/125
USPC ........................................... 358/1.15
See application file for complete search history.

(56) References Cited

U.S. PATENT DOCUMENTS

| | | | |
|---|---|---|---|
| 2006/0047538 A1* | 3/2006 | Condurso ............. | G06F 19/326 705/3 |
| 2011/0093279 A1* | 4/2011 | Levine .................. | G06F 19/326 705/2 |

* cited by examiner

*Primary Examiner* — Houshang Safaipour
(74) *Attorney, Agent, or Firm* — Kraguljac Law Group, LLC

(57) ABSTRACT

Provided are a system and method of generating a label comprising label content based on information stored by a plurality of different databases. The system includes an interface that receives an order ID. A communication system transmits the order ID over a communication network to a remotely-located terminal, and receives order data comprising information obtained from a record in a first database. A memory device that is locally connected to the interface locally stores a second database comprising rules defining requirements of a drug labeling standard. The memory device stores insufficient information to locally interpret the order ID. A label generator applies at least one of the rules using a portion of the received order data and a portion of information locally stored in the second database to control a label printer that prints the label in compliance with the drug labeling standard.

3 Claims, 5 Drawing Sheets

NETWORKABLE MEDICAL LABELING APPARATUS AND METHOD

BACKGROUND OF THE INVENTION

1. Field of the Invention

This application relates generally to a labeling apparatus for generating labels and, more particularly, a labeling apparatus and method for generating labels including a combination of: (i) information obtained from a remotely-stored database based on a machine-readable code that uniquely identifies a drug container, and (ii) information obtained from a drug formulary locally stored by the labeling apparatus.

2. Description of Related Art

Conventional labeling systems can receive data manually input by a user and use that information to retrieve detailed information about a drug from a drug database. The retrieved information is then printed onto a label that can be applied to a syringe to identify the drug that is to be administered using that syringe. Such a workflow is sufficient for labeling systems that operate as a stand-alone printing solution and locally store all of the information required to print the label for the identified drug. However, such conventional labeling systems require redundant information entry when used in environments where some of the information required to identify the drug may already be accessible to the labeling apparatus. Further, such stand-alone labeling solutions are isolated from, and incompatible with other systems employed at a healthcare facility to document drug usage. Accordingly, conventional solutions are unable to control a printing device to produce a drug label with label content specific to a drug order when the information required to produce such a label is not obtainable from one source.

BRIEF SUMMARY OF THE INVENTION

According to one aspect, the subject application involves a system for generating a label comprising label content based on information stored by a plurality of different databases, optionally stored by different memory devices. The system includes an interface that receives an order ID uniquely identifying an order for a drug to be administered to a patient. A communication system: (i) transmits the order ID over a communication network to a remotely-located terminal that has access to a first database storing a record corresponding to the order ID, and (ii) receives, over the communication network, order data comprising information obtained from the record in the first database based on the order ID. The order data is related to the order for the drug to be administered to the patient. A memory device is locally connected to the interface and locally stores a second database comprising rules defining requirements of a drug labeling standard. The requirements are to be satisfied by the label to render the label compliant with the drug labeling standard. The memory device also stores insufficient information to locally interpret the order ID. A label generator applies at least one of the rules using a portion of the received order data and a portion of information locally stored in the second database to control a label printer that prints the label in compliance with the drug labeling standard.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
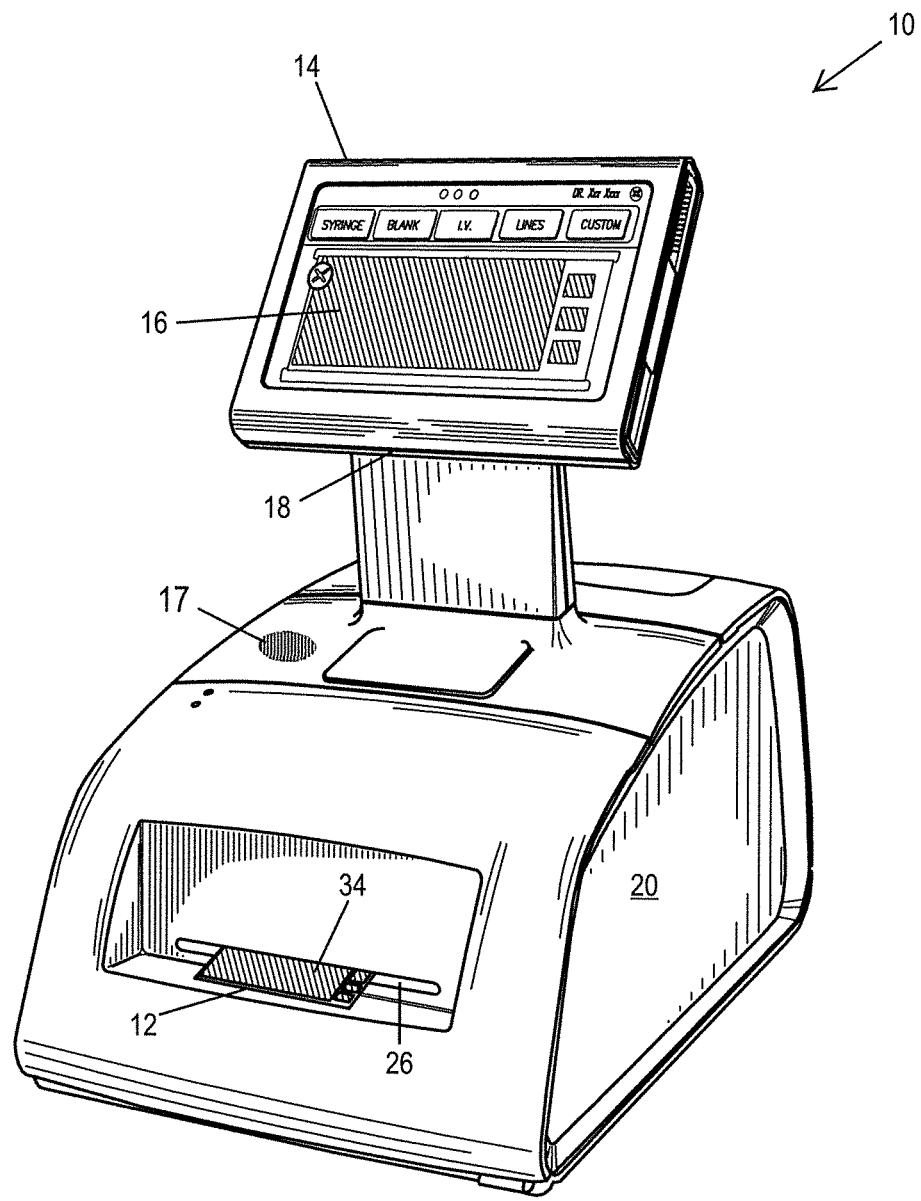
FIG. 1 shows an illustrative embodiment of a labeling apparatus for generating labels to be applied to medicinal substances in a medical facility.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

As shown in FIG. 1, the computer terminal 10 includes a touch-screen display 14 that can be pivotally coupled to a cabinet 20 to display a virtual label 16 comprising label content 34. Upon receiving approval of the label content appearing as part of the virtual label 16 as a preview, the computer terminal 10 will print the label content 34 onto a label 12 that will be applied to a delivery container (e.g., an IV bag, syringe, etc.) that is usable to administer a medicinal substance such as a drug to a patient. The computer terminal 10 can be operable to scan a computer-readable code and print a label to be applied to a medical container such as a syringe as described in U.S. Pat. No. 8,639,525 to Levine et al., which is incorporated by reference herein in its entirety. The display 14 can display soft keys that, when touched by a technician or any other user, inputs data and/or commands into the computer terminal 10, otherwise the computer terminal 10 can be provided with a pointing device (e.g., computer mouse, trackball, etc.) or other device to allow a user to input data and/or commands. The virtual label 16 is a computer-generated rendering of the label 12 that offers the user visual confirmation of the appearance of the physical label 12 to be printed by a printer 26. A computer-input peripheral such as a non-contact scanner 18 can be provided at a convenient location, such as integrally formed in a bottom portion of the display 14 to read a machine-readable code supported beneath the scanner 18 for example. Integrally forming the scanner 18 as part of the display 14 provides for space savings over an arrangement where the scanner 18 is formed as a separate peripheral, which can be repositioned relative to the display 14. However, other embodiments of the computer terminal 10 can allow for a separate and distinct scanner 18 and/or display 14.

The computer-input peripheral can be a barcode reader or radio-frequency identification ("RFID") tag reader, or any other device that reads a machine-readable code such as a barcode or RFID code, respectively, or any other machine-readable code without requiring contact between the computer terminal and the code, and optionally the user, during entry of the code. According to alternate embodiments, the display 14 can be utilized by a user as the computer-input peripheral. For such embodiments, the soft keys displayed by the display 14 can be selected to input information such as a medicinal substance being prepared to be administered to a patient or other information to be utilized in generating the label as described herein. According to yet alternate embodiments, a speaker 17 can optionally be provided to the display 14 or any other portion of the computer terminal 10 to broadcast audible sounds.

Figure 2:
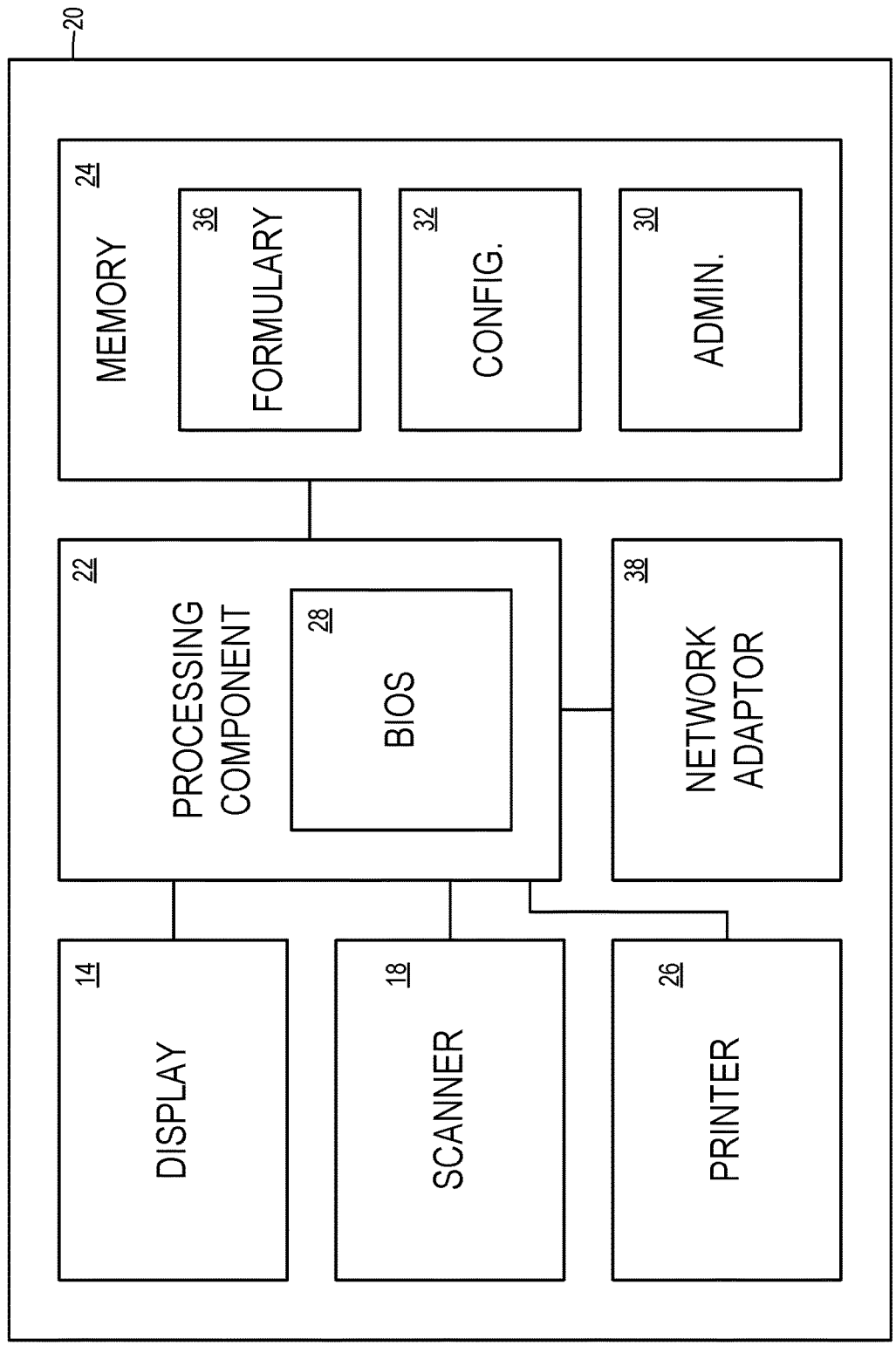
FIG. 2 shows a block diagram schematically depicting components of a labeling apparatus for generating labels to be applied to medicinal substances in a medical facility.

The computer terminal 10 also includes a cabinet 20 that houses or supports components that are operable to produce the label 12 in compliance with a medical labeling standard (e.g., The Joint Commission NPSG.03.04.01; and/or meets the intent of ISO 26825, ASTM 4774 Standards and ASA Guidelines). But if what is being labeled is anything other than the medicinal substance, then the label 12 produced is to be compliant with a standard developed by a trade or professional organization, governing body, government agency, a healthcare provider or facility such as a hospital, or any other standards body setting forth policies for labeling such material. The internal components housed within the cabinet 20 are schematically illustrated by the block diagram of FIG. 2. The components can be formed from an arrangement of computer hardware such as ASICs, computer processors, programmable logic controllers and other circuitry; or a combination of computer hardware and computer-executable instructions stored in a non-transitory computer-readable medium. For example, a processing component 22 is provided to execute computer-executable instructions stored in a non-transitory, computer-readable memory 24 such as a hard disk drive, read-only memory ("ROM"), random access memory ("RAM"), optical disc, or any other suitable memory device, or any combination thereof. The computer-executed instructions, when executed by the computer processor 22, configure the computer processor 22 as a label generator that performs the method of generating a label for a medicinal substance described in detail below. The label generator applies one or more rules defining the requirements of a drug labeling standard as described herein, to generate label content that is to be printed onto a label. The label generator controls operation of the printer 26 to produce a hardcopy of label, which can be adhesively applied to a drug container for storing the drug. A BIOS 28 is provided to load the operating system and other such administrative instructions 30 stored in the memory 24 and manage hardware interface permissions of the computer terminal 10. The operating system can be configured to only load authorized updates to prevent unauthorized changes to a formulary 36, configuration data 32 and administration instructions 30. Configuration data 32 controls various features of the computer terminal 10 that are active and available for use at any given time. The configuration data 32 can optionally be stored, updated and deleted from the memory 24 by the introduction of a so-called smart drive comprising a USB compatible flash memory to the computer terminal 10. When the smart drive is introduced to the computer terminal 10, it establishes the configuration data 32 of the computer terminal 10. The configuration data 32 can optionally be used to deactivate functional features that the computer terminal 10 would otherwise be able to perform based on the model of the computer terminal 10 purchased. Accordingly, a common hardware platform of the computer terminal 10 can be configured in a plurality of different functional configurations based on the configuration data 32.

In addition to the administrative instructions 30, the memory 24 also stores an updatable formulary 36 containing a database of medicinal substances that can be identified by the computer terminal 10 and select information for each medicinal-substance entry in the database. The formulary 36 can optionally be stored, updated and deleted from the memory 24 by the introduction of a so-called smart drive comprising a USB compatible flash memory to the computer terminal 10. When the smart drive is introduced to the computer terminal 10, it establishes the formulary 36 of the computer terminal 10. Illustrative examples of the select information that can be provided for the medicinal-substance entries includes, but is not limited to: an ID number such as a National Drug Code ("NDC"), UPC code, EAN code, or any other standard-compliant identifying data that can be used to relate a barcode or other computer-readable code to the medicinal-substance entries in the database; a unique identifier that is not standardized, but uniquely identifies a delivery container at a healthcare facility; a sound file that, when played, audibly announces the name of the medicinal substance identified in response to scanning a machine readable code; warning data; dilution data including, but not limited to, the classification of a drug as a dilution, the name of the diluent, a diluted concentration, etc.; a color code mandated by a drug labeling standard for the particular class of drugs that the medicinal substance in each entry falls into; or any combination thereof.

A network adaptor 38 is operatively connected to communicate with the processing component 22 for translating signals received by the computer terminal 10 over a network 40 (FIG. 3) at a medical facility. The network adaptor 38 can be compatible with any type of network communication. For example, the network adaptor 38 can include a hardwired, 10Base-T, 100Base-T, or 1000Base-T Ethernet interface with an RJ-45 socket, a coaxial cable interface, a fiber-optic interface, any format of wireless communication interface such as an antenna compatible with any of the 802.11 standards established by the IEEE, or any combination thereof. Embodiments including wireless network adaptors 38 can employ any desired securing protocol such as WEP, WPA and WPA2, for example, and other suitable security protocol. For embodiments including a network adaptor 38 compatible to communicate over a plurality of different network communication channels, both a hard-wired communication portion of the network adaptor 38 and a wireless communication portion of the network adaptor 38 can optionally be concurrently active. Thus, the computer terminal 10 can optionally communicate via both the hard-wired and wireless portions of the network adaptor 38 concurrently. The network 40 can include wired and/or wireless routers and switches commonly included in a local area network ("LAN"), and/or public switched communication lines (e.g., telephone lines, fiber optic cables, etc.), external servers, etc. commonly included in a wide area network ("WAN"), and any other network communication devices as required to facilitate communications between the computer terminal 10 and other devices as described herein.

Figure 3:
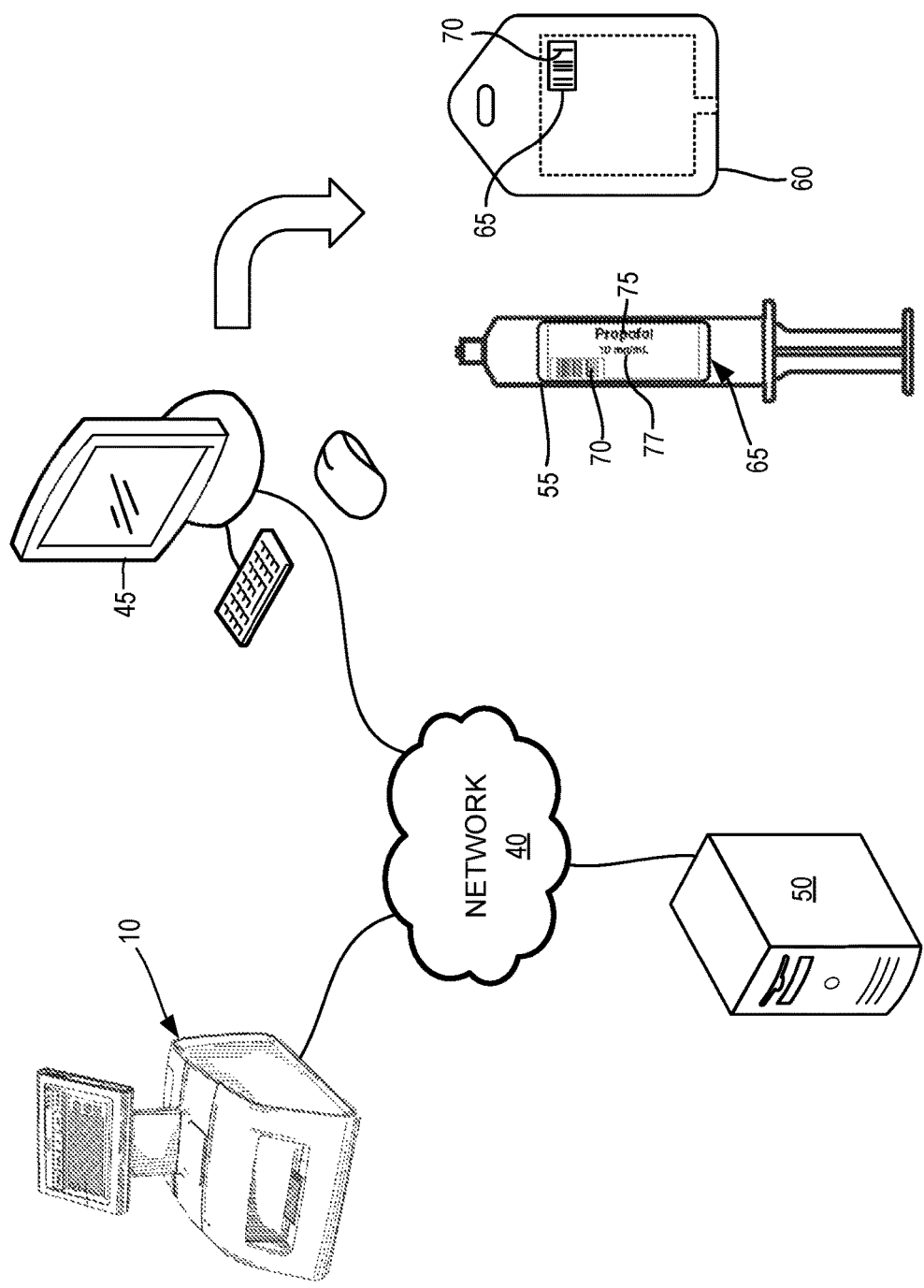
FIG. 3 shows an illustrative embodiment of a medical labeling network arrangement for preparing and labeling delivery containers with drugs at a medical facility.

As shown in FIG. 3 the computer terminal 10 can be in communication with a network 40 at a healthcare facility such as a hospital, and can communicate with other, possibly remotely-located terminals at other locations within the healthcare facility and/or external to the healthcare facility via the network 40. For example, the computer terminal 10 can be physically located within an operating room in which surgical procedures take place. A pharmacy terminal 45 can also be located within a pharmacy with a supply of drugs in the same hospital as the operating room, but at another location outside of the operating room, where drug orders can be fulfilled and drug delivery containers 55, 60 (FIG. 3) according to those orders can be prepared. Communications between the computer terminal 10 and the pharmacy terminal 45 can be established via the network 40. Further, a server 50 can also be physically located within the same hospital as the computer terminal 10, within a different building forming a portion of the same hospital system, or hosted externally of the hospital by a third party that is not part of the hospital system. Regardless of the physical location of the server 50, the server 50 is accessible to the computer terminal 10 via the network 40. The server 50 can optionally be a proprietary server, implementing security measures to limiting access to information stored by the memory of the server 50 to only authorized devices or parties with the requisite credentials. For example, the server 50 can be hosted by a third party manufacturer or proprietor of drug management, preparation and/or dispensing technologies, that is unrelated to, or unaffiliated with a manufacturer or proprietor of the computer terminal 10.

Like the computer terminal 10, the pharmacy terminal 45 and the server 50 include a processing component 22, a non-transitory memory 24 and a network adaptor 38. However, the memory 24 of the pharmacy terminal 45 and/or the server 50 can optionally lack the configuration instructions 32 and the administration instructions 30 of the computer terminal 10.

The terms "local" and "remote," when used herein to describe the storage of data, instructions or other information that can be utilized by a processing component, establish whether the stored content is stored by a memory 24 forming a part of the terminal that uses the stored content. For example, the computer terminal 10 receiving data or information stored by a remotely-located computer-readable medium of the server 50 requires the received data and/or information to be transmitted by the server 50 to the computer terminal 10 via the network 40 instead of being retrieved from a storage device physically connected directly to the computer terminal in the same physical location. In other words, receiving information from such a remotely-located device can optionally involve receiving the information from a storage device provided to a different terminal, at a different location than the computer terminal 10.

When a drug order is placed by a prescribing physician or other individual licensed or otherwise authorized to distribute a medicinal substance (which can optionally be a controlled substance), that order can be assigned a unique order identification ("order ID") that uniquely identifies that individual drug order from all other drug orders placed at a hospital, for example. The order ID can optionally be a string of numeric characters, alphabetic characters, alphanumeric characters, and optionally other characters such as symbols and/or any other ASCII characters, for example. The order ID can be assigned to a record in an electronic database accessible by the pharmacy terminal 45 via the network 40. The record in the database that is assigned the order ID can include information pertaining to the drug order, the drug prescribed, the specific drug preparation (e.g., including drugs intended for administration to a human, presented in their finished dosage form, with materials used in the preparation and/or formulation of the finished dosage form) and/or the recipient patient. For example, information included in the record includes, but is not limited to, at least one of: a prescribing physician, the recipient patient's identity (by name and/or patient ID, etc.), the drug's identity (by National Drug Code or other standardized identifier, and/or drug name, etc.), the prescribed total dose and/or total volume of the drug, the prescribed concentration of the drug, the prescribed frequency of administration of the drug, date and optionally time drug was prescribed, expiration information indicating when the prescribed drug expires relative to a time when the delivery container is prepared with the drug, the location the drug was prepared, and any other information pertaining to at least one of the drug, the prescription, the preparation, the patient and the physician.

The order ID can optionally be proprietary to the entity responsible for processing the drug order, hospital specific, or interpretable according to any metric that is not interpretable by the computer terminal 10. In other words, the computer terminal 10 can optionally be configured without the computer-executable instructions or locally stored data required to fully interpret the order ID and locally determine the information in the record assigned that order ID. However, the database record assigned the order ID that is received by computer terminal 10 from a remotely-located computer-readable medium of the server 50 can optionally lack at least a portion of the information required to publish a standard-compliant label. For example, the database record assigned the order ID can optionally lack a color code of a classification of the prescribed drug (e.g. the record lacks an indication that the color code should be blue for a narcotic according to ISO 26825 and ASTM 4774 specifications), a type of lettering commonly used for text that is to appear on the label to improve human readability of drugs with similar names (e.g. tallman lettering), etc. Accordingly, labels printed based only on information available within the database record assigned the order ID would be basic labels that are not compliant with the applicable medical labeling standard(s) and, therefore, inappropriate for use in a medical setting to label a delivery container storing the prescribed drug.

The drug order itself, or at least the order ID can be transmitted electronically via the network 40 to the pharmacy terminal 45. A pharmacist, physician, nurse, or other authorized clinician can access the drug order using the pharmacy terminal 45 to prepare a delivery container such as an IV bag 60 or a syringe 55 (FIG. 3) to contain the prescribed quantity of the drug. A basic label 65 that is not compliant with a medical labelling standard promulgated by a governing body can be printed to be applied to the IV bag 60 or syringe 55. Label content including a barcode 70 encoding the order ID or other information that can be used to retrieve information from the database record assigned the order ID can be printed onto the label 65, and the label 65 applied to the IV bag 60 or syringe 55, as appropriate. The label content printed onto the label 65 can also optionally include human-readable text 75 identifying the prescribed drug and optionally quantity information 77 indicating a dose, volume, concentration, or a combination thereof. The human-readable text 75 can be readable without the aid of a computer or other machine translator, as is utilized to interrogate and interpret the barcode 70. Further, the human-readable text 75 can include only content received as part of the order data, or content received as part of the order data as supplemented by additional data pertaining to the drug locally stored by the memory device 24. The human-readable text 75 can be printed as the label content instead of, or in addition to the barcode 70.

According to alternate embodiments, a pharmacist may prepare a collection of syringes 55 containing a drug commonly administered several times throughout the course of a day such as penicillin, for example. These penicillin syringes 55 are not affiliated with any specific drug order issued as of a time when the syringes 55 of penicillin are prepared. Again, the pharmacist or other clinician can prepare the syringes 55 of penicillin and, using the pharmacy terminal 45, print a label uniquely identifying each syringe 55 of penicillin from the other syringes 55 of penicillin and all other drug preparations. For such embodiments, when a drug order assigned an order ID is later issued for penicillin, the barcode uniquely identifying each syringe 55 of penicillin that is allocated for fulfillment of the later-issued drug order can be associated with the database record corresponding to that drug order and the corresponding order ID. Regardless of when the drug order is issued relative to preparation of the syringe 55 and/or IV bag 60, the information encoded by the barcode 70 can be utilized to retrieve information from the corresponding database record, which is not locally accessible by the computer terminal 10.

In other embodiments, a pharmacist may prepare a batch of syringes 55 containing a drug commonly administered several times throughout the course of a day such as penicillin, for example but only print a single label with an Order ID or other drug identifying information using pharmacy terminal 45 that is indicative of a batch of drugs where each syringe in the batch contains the same drug preparation. The computer terminal 10 can optionally be configured to read the Order ID or other drug identifying information from the single, non-compliant label (e.g., by scanning a barcode, reading a RFID tag, etc.) and prompt the user on display 14 to enter the number of compliant labels required and print a batch of labels for labeling the syringe 55 containers in accordance the methods described herein for producing compliant labels by scanning an Order ID on computer terminal 10.

Figure 4:
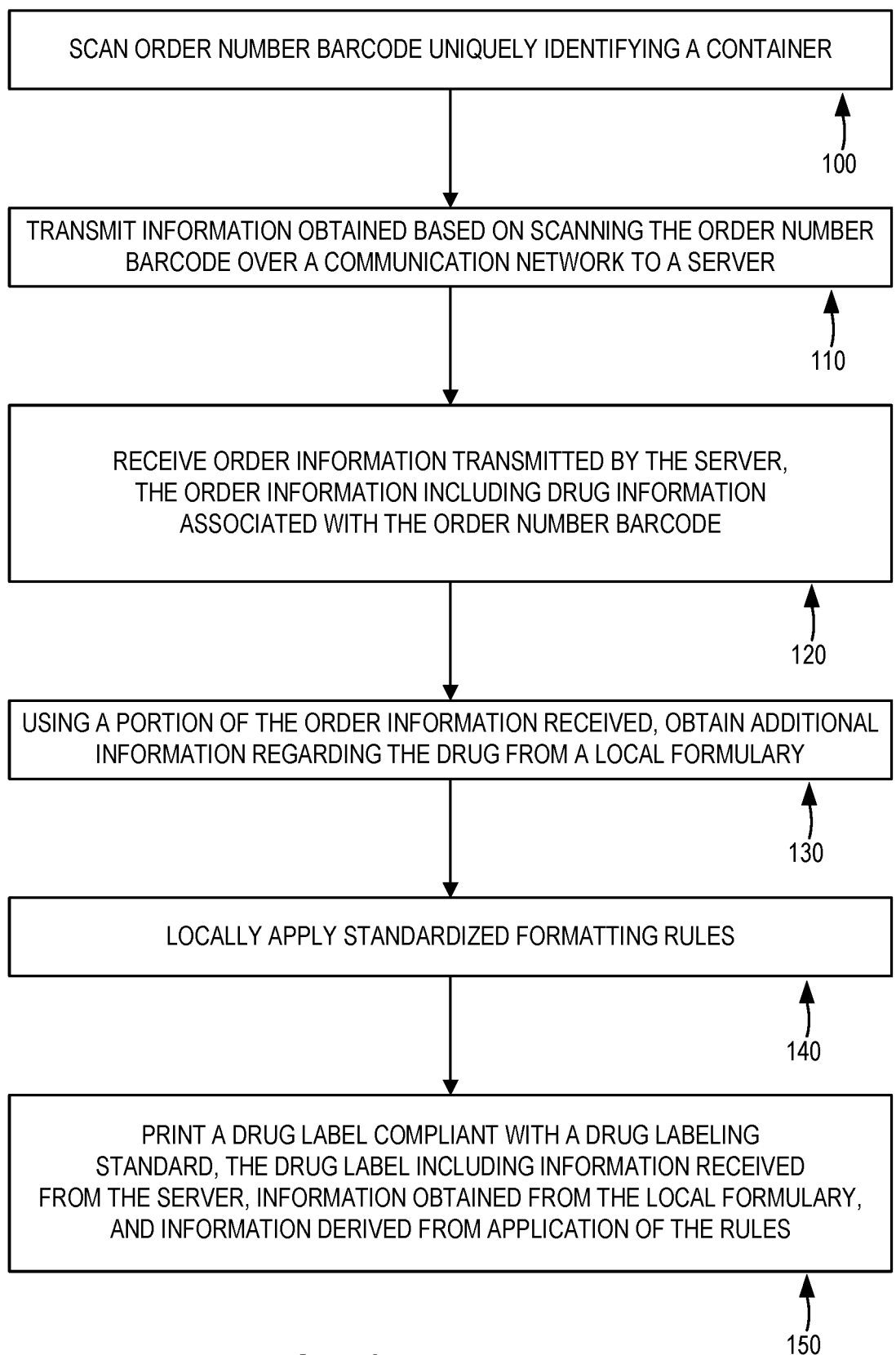
FIG. 4 is a flow diagram that schematically illustrates a process of publishing a label for a delivery container used to administer a drug to a patient.

A process of printing a standard-compliant label based on a combination of locally-accessible information and information obtained from a remotely-located terminal is depicted in the flow diagram of FIG. 4. For the sake of brevity and to clearly describe the process, publishing a standard-compliant label for a syringe 55 prepared with Fentanyl will be described, but the present disclosure is not so limited. Instead, the barcode 70 applied to any delivery container for any drug is considered to be within the scope of the present disclosure. Further, the pharmacy terminal 45 or any other device remotely located from the computer terminal 10 can optionally include the computer memory storing the database records assigned the various order ID's. But again, for the sake of brevity and clarity the process will be described with reference to the server 50 including the memory storing the database records.

The process of FIG. 4 can be performed in response to the issuance of a drug order for Fentanyl by a prescribing physician. According to the illustrative embodiment of FIG. 4, the syringe 55 including the prescribed dose of Fentanyl prepared by at the pharmacy as described above can be delivered to an operating room or other location where the computer terminal 10 is located and the drug is to be administered to the patient. The delivered syringe 55 has been prepared at the pharmacy as described above and bears the basic label 65 including the barcode 70 encoding the order ID or other information that can be used to retrieve information from the database record assigned the order ID. At step 100 in FIG. 4, the barcode scanner 18 of the computer terminal 10 is used to scan the barcode 70 uniquely identifying the syringe 55. Although the computer terminal 10 is programmed with computer-executable instructions that, when executed, cause the computer terminal 10 to decode the symbology of the barcode 70 to obtain the encoded information, the memory 24 of the computer terminal 10 does not include the database that can be referenced using the decoded information from the barcode 70. Thus, the computer terminal 10 is unable to locally obtain the required drug information to print the standard-compliant label. Accordingly, the computer terminal 10, via the network adaptor 38 (FIG. 2), transmits at least a portion of the information decoded from the barcode 70 over the network 40 to the server 50 provided with the memory storing the database including the record assigned the order ID at step 110 (FIG. 4).

At least a portion of the information included in the database record assigned to the order ID is transmitted by the server 50, and received by the computer terminal 10 at step 120. The received information can include at least one of: the drug name, the NDC of the drug, and/or any other information that can be used by the computer terminal 10 to identify the corresponding entry included in the locally-stored formulary 36. Examples of additional information that can be transmitted by the server 50 include, but are not limited to: information indicative of the identity of the person who prepared the syringe 55, information indicative of the patient's identity, the time at which the syringe was prepared, a diluent used to dilute the Fentanyl, the location where the drug was prepared, etc.

At step 130, at least a portion of the information received by the computer terminal 10 can be used to identify the entry in the formulary 36 corresponding to the drug in the syringe 55 which, in the present example, is Fentanyl. For example, information about the drug such as the lettering of the drug name "fentaNYL" on the label of syringe 55 where the final three characters "NYL" of the drug name are to appear in all caps, in accordance with a so-called tall-man lettering scheme. This information can optionally be retrieved locally from the formulary 36 by the computer terminal 10 based on information such as the NDC received from the server 50. Thus, using at least a portion of the information received from the server 50 or other remotely-located source, the computer terminal 10 can retrieve locally-stored information about the drug in question based on information encoded by the barcode 70. Without communicating with, and receiving information from the server 50, the computer terminal 10 may not be able to interpret this barcode 70 as required to retrieve the locally-stored information required by the computer terminal 10 to print a standard-compliant label 12, which can be placed over label the label 70 on the syringe 55.

Figure 5:
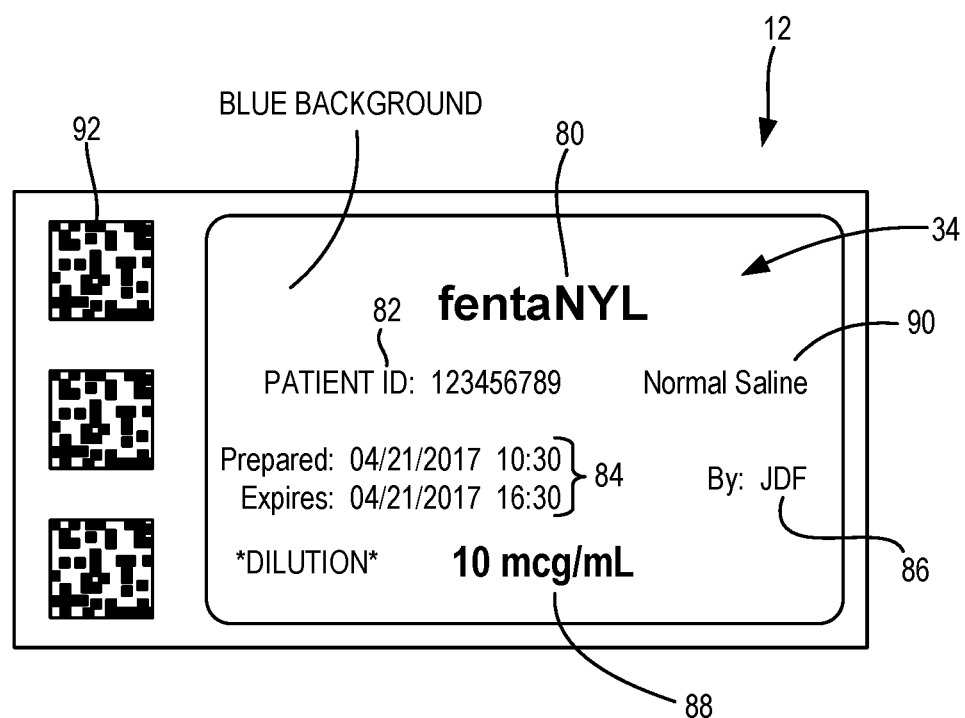
FIG. 5 shows an illustrative embodiment of a label published in accordance with an embodiment of a process described herein.

Since the database stored by the server 50 lacks formatting information required of a standard-compliant label for Fentanyl, the computer terminal 10 at step 140 can locally retrieve and apply formatting rules mandated by the standard according to which the label 12 is to comply. For example, as shown in FIG. 5, the background of the label is to be colored blue for Fentanyl. The color and/or pattern of colors on the label 12 corresponds to the classification of the drug. Referring to the current example of Fentanyl, the drug is classified as a narcotic and standards such as ISO 26825 and ASTM 4774 for example, specify the color blue is used on the label to identify a narcotic. The NDC received from the server 50 as part of the information associated with the Order ID is used to retrieve information from the formulary 36 stored locally in computer terminal 10 that includes the information specifying the classification of the drug. Rules configured in computer terminal 10 use the drug classification to print the color and/or pattern of colors on the label and the format of the label content 34 to fit on the physical label. At step 150 in FIG. 4, the computer terminal 10 prints the label content 34 onto the label 12 to publish the standard compliant label shown in FIG. 5. The label content can include information received from the server 50, information retrieved locally from the formulary 36, information derived from application of the rules applied at step 140, or a combination thereof. As shown in FIG. 5, the resulting standard-compliant label 12 includes a blue background as mandated by the standard for drugs such as Fentanyl, the drug name 80 in tall-man lettering, the patient ID 82 in an obfuscated format (e.g., as a patient number instead of the printed name of the patient), expiration information, information indicative of the person who prepared the syringe 55, the concentration 88 of the drug in the syringe 55, and the diluent 90 used to prepare the dilution. Additionally, the computer terminal 10 can print a barcode 92, optionally redundant barcodes 92, encoding at least one of: a portion of the label content 34, at least a portion of the information decoded from the barcode 70, at least a portion of the information received from the server 50.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system for generating a label comprising label content based on information stored by a plurality of different databases, the system comprising:
    an interface that receives an order ID that uniquely identifies an order for a drug to be administered to a patient;
    a communication system that: (i) transmits the order ID over a communication network to a remotely-located terminal that has access to a first database storing a record corresponding to the order ID, and (ii) receives, over the communication network, order data comprising information obtained from the record in the first database based on the order ID, wherein the order data is related to the order for the drug to be administered to the patient;
    a memory device that is locally connected to the interface and locally stores a second database comprising information and rules defining requirements of a drug labeling standard, the requirements of the drug labeling standard comprising a color code that is required to appear on the label to identify a class of the drug to be administered to the patient, but is missing from the order data received by the communication system, wherein the requirements are to be satisfied by the label to render the label compliant with the drug labeling standard, and wherein the memory device stores insufficient information to locally interpret the order ID; and
    a label generator that supplements the order data received by the communication system with information about the color code included in the second database that is missing from the order data, and applies at least one of the rules using a portion of the received order data and at least the information about the color code locally stored in the second database to control a label printer that prints the label in compliance with the drug labeling standard.

2. The system of claim 1, wherein the at least one of the requirements of the drug labeling standard that is missing from the order data is formatting information defining a format of content that is to be printed onto the label.

3. The system of claim 1, wherein the label generator supplements the received order information with additional information about the drug retrieved from the memory device, and produces the label to include the received order information as supplemented by the additional information.

* * * * *